(12) United States Patent
Green et al.

(10) Patent No.: US 9,267,951 B2
(45) Date of Patent: Feb. 23, 2016

(54) MICELLAR COMPOSITIONS FOR USE IN BIOLOGICAL APPLICATIONS

(75) Inventors: Mark Green, London (GB); Philip Howes, Huntingdon (GB)

(73) Assignee: King's College London, London (GB)

( * ) Notice: Subject to any disclaimer, the term of this patent is extended or adjusted under 35 U.S.C. 154(b) by 0 days.

(21) Appl. No.: 13/499,098

(22) PCT Filed: Sep. 28, 2010

(86) PCT No.: PCT/GB2010/051620
§ 371 (c)(1),
(2), (4) Date: Jul. 9, 2012

(87) PCT Pub. No.: WO2011/039535
PCT Pub. Date: Apr. 7, 2011

(65) Prior Publication Data
US 2012/0269736 A1    Oct. 25, 2012

(30) Foreign Application Priority Data

Sep. 29, 2009   (GB) .................................. 0917097.8

(51) Int. Cl.
| | | |
|---|---|---|
| *A61K 49/00* | (2006.01) | |
| *G01N 33/58* | (2006.01) | |
| *A61K 49/18* | (2006.01) | |
| *B82Y 5/00* | (2011.01) | |

(52) U.S. Cl.
CPC .......... *G01N 33/586* (2013.01); *A61K 49/0002* (2013.01); *A61K 49/0019* (2013.01); *A61K 49/0054* (2013.01); *A61K 49/0082* (2013.01); *A61K 49/1806* (2013.01); *A61K 49/1818* (2013.01); *B82Y 5/00* (2013.01)

(58) Field of Classification Search
CPC .................................................. A61K 49/0002
See application file for complete search history.

(56) References Cited

U.S. PATENT DOCUMENTS

| | | | |
|---|---|---|---|
| 6,022,500 | A | 2/2000 | John et al. |
| 2004/0109824 | A1* | 6/2004 | Hinds et al. .................. 424/9.32 |
| 2006/0100696 | A1* | 5/2006 | Atanasoska et al. ......... 623/1.44 |
| 2009/0036625 | A1 | 2/2009 | Chang et al. |
| 2009/0098206 | A1* | 4/2009 | Kessell et al. ................. 424/489 |

OTHER PUBLICATIONS

Abdelaal, International Journal of Polymeric Materials, 2005.*
Janjic et al., "Self-delivering nanoemulsions for dual fluorine-19 MRI and fluorescence detection," Journal of the American Chemical Society, Mar. 5, 2008, vol. 130, No. 9, pp. 2832-2841.
Nitin et al., "Functionalization and Peptide-Based Delivery of Magnetic Nanoparticles As an Intracellular MRI Contrast Agent," Journal of Biological Inorganic Chemistry, Jun. 30, 2004, vol. 9, No. 6, pp. 706-712.
Kim et al., "Magnetomicelles: composite nanostructures from magnetic nanoparticles and cross-linked amphiphilic block copolymers," Nano Letters American Chem. Soc USA, Oct. 2005, vol. 5, No. 10, pp. 1987-1991.

(Continued)

*Primary Examiner* — Paul Dickinson
(74) *Attorney, Agent, or Firm* — Stites & Harbison, PLLC; Mandy W. Decker

(57) ABSTRACT

This invention relates to a composition comprising a micelle for use in biological applications, the micelle comprising: a substantially water-insoluble conjugated polymer which exhibits luminescence or fluorescence from about 300 nm to about 1500 nm of the electromagnetic spectrum: a biocompatible surfactant and/or lipid: and a MRI active agent.

24 Claims, 2 Drawing Sheets

(56) References Cited

OTHER PUBLICATIONS

Figure 1:
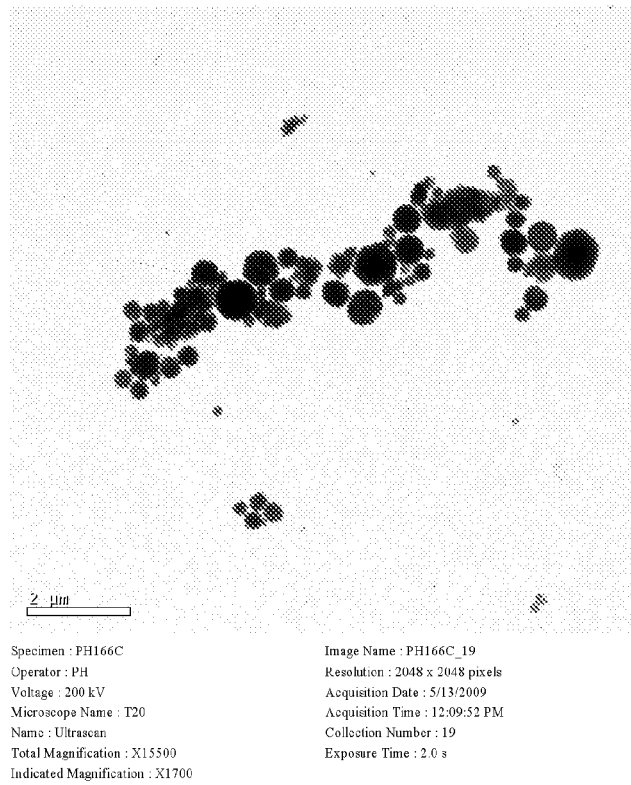

Green et al., "Simple conjugated polymer nanoparticles as biological labels," Proceedings of the Royal Society A: Mathematical, Physical and Engineering Sciences, Sep. 8, 2009, vol. 465, No. 2109, pp. 2751-2759.

Howes et al., "Synthesis, characterisation and intracellular imaging of PEG capped BEHP-PPV nanospheres," Chemical Communications, May 14, 2009, No. 18, pp. 2490-2492.

EPO/ISA, International Search Report for international application No. PCT/GB2010/051620, mailed Mar. 18, 2011.

* cited by examiner (a)      (b)      (c)      (d)

MICELLAR COMPOSITIONS FOR USE IN BIOLOGICAL APPLICATIONS

The invention relates to micellar compositions for use in biological applications; more specifically to micellar compositions for use in the labelling of biological material for biological imaging procedures, and in the detection of substances.

The use of nanotechnology for biological applications is a popular area of research. Nanoparticles are used in a wide range of fields, from drug delivery to photodynamic therapy. However, to date their use in biological imaging and in substance detection has been limited. One reason for this may be the lack of non-toxic particles with multi-modal imaging capabilities.

Biological imaging is a vital tool in biotechnology and biological sciences, as well as in medicine. Any biological material can be imaged, either in vitro or in vivo. Applications for fluorescent labelling includes technologies such as medical and non-medical fluorescence microscopy, histology, flow cytometry, fluorescence in-situ hybridization (medical assays and research), DNA sequencing, immunoassays, binding assays and separation.

The labelling of samples of biological material is commonly carried out in vitro in order, for example, to determine metabolic pathways.

In medicine, biological imaging enables the facile monitoring of physiological functions of a patient to ascertain their precise condition and to minimize the risk of serious illness brought about by clinical, physiological, and pathological conditions. Compounds which absorb and emit light in the visible and near-infrared regions of the electromagnetic spectrum are used for a number of medical applications due to their biocompatibility, high molar absorption, or high fluorescence quantum yields. High optical sensitivity in conjunction with these compounds as contrast agents permits visualization of organs and tissues without the undesirable effects of ionizing radiation.

Conventionally, such fluorescence labelling involves the use of an organic dye molecule bonded to a moiety which, in turn, selectively binds to a particular biological system, the presence of which is then identified by excitation of the dye molecule to cause it to fluoresce.

The majority of existing biological labels are monomeric organic dyes, such as fluorescein and indocyanine green. However, these compounds exhibit instability under photoexcitation and fade quickly, usually within minutes or hours of being opened and exposure to aerobic conditions.

Organic dye nanoparticles, i.e. quantities of the organic dye contained within a carrier such as a polymer, have been prepared and used in simple biosensing, as opposed to biolabelling. The preparation of non-luminescent nanoparticles that host luminescent dyes mostly involves the use of common dyes, e.g. fluorescein or monomeric ruthenium-containing dyes, in polymeric materials such as poly(methyl methacrylate) (PMMA). Such nanoparticles have been used in DNA microarrays. Nanoparticles of non-luminescent polymers such as polyetherimide (PEI) have been made and linked with organic dyes, and used in apoptosis imaging. However, the chemistry is difficult and a specific polymer is required for any particular organic dye to function.

Labelling has also been carried out using monomeric transition metal complex-containing dye molecules in silica spheres. Dye molecules such as tris(2,2'-bipyridyl)osmium (II) bis(hexafluorophosphate) (OsBpy), tris(2,2'-bipyridyl) dichlororuthenium(II) hexahydrate (RuBpy), 5-fluorescein isothiocyanate (5-FITC), 5-carboxyrhodamine 6G, succinimidyl ester (5-CR6G, SE), 6-carboxy-X-rhodamine, and/or succinimidyl ester (6-ROX, SE) are used, embedded in a non-luminescent silica particle (WO 2007/044712 and WO 2007/044711). Complexes of this type are commercially available from Life Science Inc., (www.lifesci.com). These complexes use dyes as fluorescent markers, and suffer from the same limitations as dyes in that they degrade quickly offering poor visualisation stability.

Other approaches have been to use the monomeric fluorescent dye N-(2,6-diisopropylphenyl)perylene-3,4-dicarboximide (PMI) as a lumiphore in nanoparticles of, for example, polystyrene. This is similar to the work described above, i.e. incorporating a monomeric dye inside an inert non-luminescent nanoparticle.

More recently, nanoparticles of conventional inorganic semiconductors such as CdSe (also known as quantum dots) have found applications in biological imaging. Their narrow, bright emission and increased stability make them into candidates to replace organic dyes used in imaging applications. Functionalisation of the nanoparticle surface with a biologically compatible ligand such as a protein allows linking to various biological moieties, and this technology has been used in oncology surgery, in vivo imaging, blood flow monitoring and standard cell imaging. However, publications have shown that these materials are cytotoxic due to the cadmium content of the emitting particles (Nano Letter, 2004, 4, 11; Chem Commun, 2005, 121; Nano Letter, 2005, 5, 331; Microbiol, Immunol, 2004, 48, 669).

Additionally, the water-soluble quantum dots are prepared via phase transfer of pre-made nanoparticles. This is a two-step process. The initial step (the synthesis of the nanoparticles) requires organometallic/inorganic precursors, an organic solvent, high temperatures, and up to several days of synthesis under a nitrogen atmosphere. The resulting particles are soluble in non-polar organic solvents. The second step involves a phase transfer, by adding a polar capping agent to the surface or wrapping the particles in a water soluble material to form a micelle. These are time-consuming and far from straightforward synthetic conditions. There is also the risk that the luminescence properties may be lost as a result of the reaction.

Light-emitting polymers (LEPs) are substantially water-insoluble conjugated polymers which function as organic semi-conducting materials and have been known for some time. They have been studied in depth and their physical characteristics are understood. They are stable under harsh conditions (e.g. they are able to withstand electrical currents for hundreds of hours), many of them are commercially available, and they are commonly used in solid-state devices such as diodes and displays, solar energy applications and printable electronics. However, LEPs are substantially insoluble in water or aqueous solvents as they do not posses the required linking groups for bioconjugation or water solubilisation. This renders them useless for biological applications such as labelling.

Despite this, LEPs have been examined as potential biological probes. Attempts to overcome the insolubility problem have involved the functionalisation of LEPs by, for example, polar or charged groups or a water-soluble side group, after it was suggested that convenient LEPs such as the PPV (poly(phenylene vinylene)) family of materials could be useful if a side group (usually ionic) were added to induce water-solubility (P. S. Heeger, PNAS, 1999, 96, 12219). However, functionalising LEPs in this way also has a significant and detrimental impact upon their optical properties and sensitivity by, for example, causing a drop-off in quantum yield, or causing the polymer to precipitate out of solution.

This is thought to be due to a conformational change of the polymer which is brought about by the functionalisation. The optical properties are dependant upon the side groups on the LEPs, so the addition of biologically-desirable side groups, such as a carboxylic acid, amine or thiol, or more specific units such as biotin and antibodies will introduce functionalities which will radically alter the composition of the light emitting species.

Additionally, the functionalised LEPs are not commercially available and have to be individually prepared. This preparation is difficult as the functionalisation is hard to control and often leads to non-specific binding. As a result, the preparation is not readily available to non-chemists such as biology-trained imaging scientists.

Furthermore, when a functionalised LEP is used as a biological probe, it is the quenching of the LEP emission which is the indicator of biological activity, and not the emission itself (e.g. Chen et al, PNAS, 1999, 96, 12287). When a probe including a functionalised LEP is introduced into a system comprising a biological material, the emission is quenched upon the functionalised LEP binding to the targeted biological material. Hence, a functionalised LEP acts as a sensor for the biological material and not as a label. It is therefore only of use in determining the presence of a biological material, but not how much biological material there is, nor its precise nature. For example, it might be possible to identify the presence of cancer cells using a functionalised LEP, but not how many cells there are, how widespread they are, nor their activity.

Similar work has been reported using specifically designed and synthesised polyelectrolytes such as poly[lithium 5-methoxy-2-(4-sulfobutoxy)-1,4-phenylenevinylene] (MBL-PPV) (Wang et al, PNAS, 2002, 99, 49; Ambade et al, Polymer International, 2006, 56, 474), which shows enhanced emission when bound to a specific protein. Non-specific binding was also observed, as well as quenching. In every case, the LEP had to be chemically modified to be fit for purpose. Again, the functionalised LEPs were not used as biological labels, but as biological sensors. The sensing was achieved in solution by observing the effect of biological material on the photoluminescence. As above, the effect monitored is the quenching of the LEP emission and not the emission itself.

Typically in biolabelling, the imaging compound or composition is added to a biological material and the subsequent emission is imaged and monitored via microscopy. The presence of the emission is key to the function of the label, whilst an absence of emission (due to e.g. quenching) provides no useful information to a user.

In quenching experiments, such as those mentioned above, any detection would be done in a test tube or luminescence cuvette. It would not be possible to actually 'see' anything using eyes or a microscope as the quenching is monitored using a spectrometer. In labelling, a microscope or charge-coupled device (CCD) camera is required to observe the emission.

WO 01/27625 (Leif et al) describes the use of tagged peptides or synthetic polymers in biological labelling, the labels include optical, paramagnetic or radioactive species. Detection of the analyte is via interaction with side chains extending from the polymer.

Conjugated LEPs with ionic side groups (normally cationic, although anionic species have also been used) have been used extensively in DNA assays, using the changing optics to sense interactions with biological materials. Again, these sensing applications are different from labelling, as the biological material is not imaged and any data acquired is based on the alteration of the LEP optics, notably shifts in the emission or absorption intensity or spectral position. A non-ionic approach has also been developed to produce a water-soluble conjugated LEP, by grafting on hydroxyl side groups. Unfortunately, the new side group quenches the emission quantum yield, and this product has not been used in biological labelling or sensing (Kuroda and Swager, Chem. Commun., 2003, 26).

There is only one example of an LEP being used as a biological label, in the labelling of bacteria (JACS, 2004, 126, 13343). Again, this is a functionalised LEP which has been specifically synthesized for the task. Using the reported method, one could not choose to label the bacteria with different labels emitting different colours, as a user would be significantly restricted in the labels which could be used as only one polymer can be used to label any given bacteria.

Other attempts have been made to modify LEPs:

MEH-PPV (poly[2-methoxy-5-(2'-ethyl-hexyloxy)-1,4-phenylene vinylene]) has been dispersed in water by sonicating a THF solution of it in water. The resulting material resembled a network of nanowires which was unsuitable for labelling applications as the network covered large areas and provided no anchor point for further conjugation.

Nanofibres of MEH-PPV have been obtained by electro-spinning; the long fibres obtained are unsuitable for labelling applications as they are too long and provide no method of bioconjugation nor well defined surface chemistry.

Oligofluorenes were condensed into nanoparticles containing water-soluble side chains, but were not used in labelling.

As yet, there is no LEP available that is able routinely to bind to biological material and which does not quench, with one exception where the LEP instead precipitated out of solution.

It would be desirable to provide a multi-modal labelling composition. Such compositions offer benefits including superior visualisation of the biological process of interest, the associated improvement of information collected, and reduced cost/patient distress by improving and speeding up the diagnostic process. For instance, a single application of such a composition could be used in more than one different diagnostic procedure, making diagnosis less arduous for the patient. The use of such compositions would also result the need to complete fewer invasive procedures as the improved visualisation of the labelled process would reduce the need for surgery. Improved prediction and detection of disease, and more reliable monitoring of therapeutic outcomes could also be offered, helping to match individual patients with the most appropriate therapy at the earliest juncture, thereby avoiding the need to wait for often delayed clinical response assessment of therapy.

Multimodal nanomaterials which may exhibit both MRI and optical activity have been reported previously. Semiconductor quantum dots have been physically linked with $Fe_3O_4$, and are often described as "dimers" or "heterofunctional nanomaterials" (Gao et al, J. Am. Chem. Soc., 2008, 130, 3710; McDaniel et al. ACS Nano, 2008, 3, 434; Tamil Selvan et al., Angew. Chem. Int Ed, 2007, 46, 2448; and Shi Et al., Adv. Mater., 2006, 18, 1889). In each case a semiconductor nanoparticle has been grown on top of a magnetic nanoparticle (or vice versa), or grown in a dumbbell type structure. In other cases, preformed semiconductor quantum dots and magnetic particles have been mixed together. In all cases involving the use of quantum dots, the potentially toxic elements of cadmium or lead are present in the quantum dots as the key emitting material.

MRI active complexes have also been added to semi-conducting quantum dots; however, these systems incorporate cadmium selenide as the emitting core. $NaYF_4$ doped with a rare-earth has been used as an alternative; however, the inclusion of fluorine in such systems is undesirable due to the potential toxicity of this anion upon complex breakdown. MRI active agents and luminescent dyes have also been combined, however, such mixtures are negatively effected by the presence of the dye, and the tendency of these to fade rapidly upon photo-excitation (Lim et al, Small, 2008, 4, 1640; Kim et al., Angew Chem. Int. Ed, 2008, 47, 8438; and Kircher et al., Cancer research, 2003, 63, 8122.).

Other work in the field of multi-modal imaging has involved the combination of quantum dots and dyes (such as ruthenium or organic dyes); mixtures of fluorescent and other dyes; and mixtures of quantum dots, phosphorescent compounds and/or dyes.

WO 2007/027159 (Chen) describes the use of conjugated organic polymers as biological labels. These polymers are entangled with an amphiphilic molecule to render the polymer soluble in aqueous environments. However, there is no disclosure in Chen of a micellar structure, or of the use of more than one imaging agent, to form a multimodal composition.

Micellar structures are useful candidates for inclusion in such multimodal compositions as numerous functionalities can be engineered into one particle. To date, no effective nano-sized multimodal particles have been made commercially available despite the benefits provided.

Dubertret et al. have attempted to make biological labels using quantum dots of CdSe/ZnS encapsulated by a lipid membrane (Dubertret et al, Science, 2002, 298, 1759.). Similarly, Park et al. have made a multimodal imaging agent comprising cadmium containing quantum dots encapsulated by a phospholipid micelle (J. H. Park, et al. Angew. Chem Int. Ed., 2008, 47, 7284.). Both of these imaging agents present toxicity problems when used with biological systems.

There are currently deficiencies in the ability to detect substances at, for instance, crime scenes. Forensic scientists often find fingerprints and biological substances at the scene of a crime. Currently, forensic examiners initially search for signs of blood, semen and saliva with the naked eye. This is followed by examination using specialised light sources. Semen and saliva exhibit fluorescence under some, but by no means all, circumstances. Blood has no native fluorescence but does have a strong absorption band centred around 415 nm. Hence it can be "visualised", under light sources as a dark spot against a lighter background. This does not work on many substrates, and/or when minute spots of blood are present or when the perpetrator of a crime has tried to clean-up traces. Where visual and light source inspection has failed to indicate the presence of body fluids, scene examiners rely on submission of "best estimate" evidence, submitting items for further examination which they think may be a source of DNA (e.g. underwear, cigarette butts etc.). These approaches often fail to detect traces of body fluids. Even if visual or light source examination has revealed what may be blood, semen or saliva, this is presumptive and further colorimetric and, in the case of presumptive semen, microscopical tests are required to confirm the presence of the various fluids. A separate test is required for each body fluid, with different procedures and reagents used for each. There is thus a desire to create a test which can more readily detect one or more substances that may derive from a human, such as saliva, blood, semen and metabolites.

Fingerprint identification is one of the cornerstones of forensic evidence. However, currently a fingerprint is useful solely when police or other security agencies are able to obtain a positive match with those prints present on databases.

When visualised under a microscope, the skin on the palms and fingers appear as ridges and grooves. It is the pattern of these friction skin ridges that produces the unique fingerprint. Each skin ridge has a single row of pores, through which sweat is excreted and deposited on the surface of the skin. When a finger touches a surface, sweat is deposited leaving an impression of the finger's ridge pattern, referred to as a latent fingerprint. Such fingerprints are considered 'invisible prints' as they require physical or chemical treatments to enable visualisation.

Sweat is the ultrafiltrate of blood plasma, containing inorganic ions, lactate, urea and amino acids and these species are therefore present within a freshly deposited fingerprint. In addition, it is known that orally ingested and metabolised drugs are excreted in sweat. These drugs have been measured in sweat through the use of collection devices, such as patches of adsorbent cotton, followed by extraction and subsequent analysis using techniques such as gas chromatography coupled with mass spectrometry (GC-MS) detection. However, the methods are laborious, require a large amount of sweat collected over a period of time and are therefore not suitable for rapid analysis, for example roadside testing of persons suspected of driving under the influence of drugs. The detection of substances in fingerprints has not been possible using the methods of the prior art because of the small quantity of the substances in the fingerprint.

It would therefore be desirable to provide a composition which can be used to detect substances such as sweat, blood, semen, and/or saliva in a rapid, repeatable manner, if possible at a crime scene or in another non-laboratory setting. A composition which could report the detection of the substance in a multi-modal manner, and/or which could separate the substance from the substrate on which it is found, for later detailed analysis in the laboratory or to concentrate the sample on site for easier visualisation would also offer an improvement over known crime scene detection compositions.

The invention aims to overcome or ameliorate one or more of the problems described above.

Therefore, in accordance with a first aspect of the invention, there is provided a composition comprising a micelle for use in biological applications, the micelle comprising:
a substantially water-insoluble conjugated polymer which exhibits luminescence or fluorescence from about 300 nm to about 1500 nm of the electromagnetic spectrum;
a biocompatible surfactant and/or lipid; and
an MRI active agent.

The compositions described above have the advantages of being water-soluble and non-toxic (being free of substances such as cadmium which are often used in known labelling and detection compositions) allowing their use in the labelling of biological material, their use in biological applications or in medical diagnosis or therapy. They are particularly suitable for use in biological imaging, and in the detection of substances, in particular in during crime scene investigations. The compositions of the invention have the additional advantage that they are generally stable and can be used without the need for any complex chemical functionalisation to impart water-solubility. This improves the accessibility of the compositions, as the user need not be a skilled chemist in order to prepare the inventive compositions. Further, the three components of the micelles are inexpensive, allowing an affordable commercial product to be produced.

Accordingly, there is provided in a second aspect of the invention a method of labelling a biological material, comprising the steps of: providing a composition according to the first aspect of the invention; and bringing the composition into contact with the biological material.

A third aspect provides for the use of a composition according to the first aspect of the invention in the labelling of biological material for imaging.

The composition, method and use are particularly of advantageous when the biological application is the labelling of biological material for imaging, which may be carried out either in vivo or in vitro.

According to a fourth aspect of the invention, there is provided a biological material labelled by a composition according to the first aspect of the invention.

There is also provided in a fifth aspect of the invention, a composition as described in the first embodiment of the invention, for use in medical diagnosis or therapy.

A sixth aspect of the invention provides a method for the detection of a substance, the method comprising: providing a composition according to the first aspect of the invention; contacting the composition, which may or may not have the substance on its surface, with the composition; optionally removing the composition from the substrate; and fluorescent and/or magnetic resonance imaging the composition to determine whether the substance was present on the substrate.

In the invention, by "micelle" is meant a substance comprising a polymer which is substantially encased (usually entirely encased) within a biocompatible surfactant and/or lipid, to form a "core-shell" structure in which the polymer forms the core of the micelle and the biocompatible surfactant and/or lipid a distinct, encapsulating, shell around the core.

By "substantially water-insoluble" is meant that the polymer is soluble in an aqueous solvent at no more than about 30 µg/ml at ambient temperature, preferably no more than about 25, 20 or 15 µg/ml.

By "polymer" it is intended to mean a compound comprising at least 5 monomer units, including homopolymers and copolymers.

By "conjugated polymer" it is intended to mean any polymer which has alternating single and double bonds between carbon atoms on a polymer backbone.

By "biocompatible surfactant and/or lipid" it is intended to mean any surfactant or lipid which is substantially soluble in water or aqueous solution and does not cause toxic effects to biological material.

By "biological material" is meant any tissue or cell material which is capable of being bound to or interacting with a biocompatible surfactant and/or lipid. Exemplary biological material includes, but is not limited to, proteins, polypeptides, nucleic acids, cancer cells, organ tissue such that of a heart, liver or kidney, skin, blood or normal cells. The compositions of the invention are able to be used as direct replacements for any existing biological label which is used in the analysis of biological material, either in a human or animal subject or in a sample which has been taken from a human or animal subject. In many instances the biological material binds to the biocompatible surfactant and/or lipid, facilitating labelling, or detection and separation, but certain biological materials, such as blood, are capable of effectively absorbing and encapsulating the composition of the invention.

By "substance" is meant any compound, whether organic or inorganic, to be detected. In general the substances of interest in the detection methods of the invention are biological substances such as semen, blood, saliva, hormones and sweat; and other substances such as drugs, drug metabolites and explosives.

By "biocompatible surfactant and/or lipid" it is intended to mean any surfactant or lipid which is substantially water-soluble and does not cause any significant toxic effects to biological material.

While functionalised substantially water-insoluble conjugated polymers such as LEPs have been used in biological applications as described above, compositions comprising a micelle of such a polymer and a biocompatible surfactant and/or lipid have not. Using the composition of the invention, a substantially water-insoluble conjugated polymer can be used in biological labelling either in vivo or in vitro without the need to functionalise it beforehand to impart water-solubility. Further, the presence of the MRI active material, in addition to the light emitting polymer, offers the possibility of multiple detection methods from a single micelle.

According to the invention, any commercially available substantially water-insoluble conjugated polymer can be made water-soluble and biologically-compatible by being enveloped in a water-soluble biocompatible surfactant and/or lipid to create a micelle. Upon reaction with the water-soluble biocompatible surfactant and/or lipid, the conjugated polymer folds back on itself, enabling it to be encased by the surfactant or lipid. This results in a polymer particle encased with the surfactant or lipid whilst maintaining its emissive properties and providing a water-soluble shell with a surface chemistry available for further conjugation.

In this manner, by virtue of the water-solubility imparted upon it by the biocompatible surfactant and/or lipid, any simple commercially available substantially water-insoluble conjugated polymer, such as MEH-PPV, can be used in water and used in labelling experiments instead of less stable ordinary dyes (which might fade or bleach) or quantum dots (which commonly contain toxic cadmium), or polymers which first required a complex functionalisation to impart water solubility. The known emission properties of the commercially available substantially water-insoluble conjugated polymers are not compromised or lessened as there is no need to functionalise them. When such polymers are functionalised, it is not possible to be certain of the impact it will have on the emission properties.

Furthermore, commercially available substantially water-insoluble conjugated polymers are relatively cheap, and the resulting material can be used in labelling, detection and/or separation experiments without the need to alter microscope optics or labelling techniques or protocols. The invention therefore exploits the science of substantially water-insoluble conjugated polymers designed for optoelectronic applications and utilises these materials in bioimaging, without the need for any chemical alteration of the polymer itself, or of the MRI active agent with which is it mixed in the core. Surprisingly, the emission strength of the conjugated polymers is barely diminished by being enveloped in a micelle, and a strong emission signal is still given out and detected.

Also, in contrast to the laborious conditions required for the preparation of the quantum dots described above, the composition used in the invention is simple to prepare as the reactants—the substantially water-insoluble conjugated polymer, the biocompatible surfactant and/or lipid, and the MRI active agent—are mixed and only require sonicating for a relatively short period of time, such as up to about 2 hours. This is only a one-step reaction, and does not require the use of air-sensitive solvents, elevated temperatures or prolonged reaction times. The method of preparation used is similar to that described by Landfester et al (Adv. Mater., 2002, 14, No. 9, May 3), which is incorporated herein by reference in its entirety.

It will be appreciated by those skilled in the art that the numerous conjugated polymers available and used in light-emitting diodes can be used in accordance with the invention, particularly those which emit in the visible and infra-red regions of the electromagnetic spectrum. Polymers may be used alone, or in combination in the core of the micelles of the invention, often only one polymer will be present, although two, three or four may also be used. Exemplary polymers which may be of use in the invention include, but are not limited to:

Poly[9,9-di(3',7'-dimethyloctyl)fluoren-2,7-yleneethynylene]
Poly[9,9-didodecylfluroenyl-2,7-yleneethylnylene]
Poly[9,9-di(2'-ethylhexyl)fluoren-2,7-yleneethynylene]
Poly(9,9-dioctylfluorenyl-2,7-yleneethynylene
Poly[9,9-bis-(2-ethylhexyl)-9H-fluorene-2,7-diyl]
Poly(9,9-dihexyl-9H-fluorene-2,7-diyl)
Poly(9,9-di-(2-ethylhexyl)-9H-fluorene-2,7-diyl)
Poly[(9,9-di-(2-ethylhexyl)-9H-fluorene-2,7-diyl)-co-(1-methoxy-4-(2-ethylhexyloxy)-2,5-phenylenevinylene)]
Poly[(9,9-dihexyl-9H-fluorene-2,7-diyl)-co-(1-methoxy-4-(2-ethylhexyloxy)-2,5-phenylenevinylene)]
Poly(2,5-bis(1,4,7,10-tetraoxaundecyl)-1,4-phenylenevinylene)
Poly(2,5-dioctyl-1,4-phenylenevinylene)
Poly(2,5-dioctylphenylene-1,4-ethynylene)
Poly[1,2-bis(benzylthio)acetylene]
Poly[1,2-bis(ethylthio)acetylene]
Poly[bis(methylthio)acetylene]
Poly(3,5 pyridine)
Poly(3-(2-methoxyethoxy)ethoxymethylthiophene-2,5-diyl)
5,5'-Dibromo-2,2'-bithiophene
Poly(3-butylthiophene-2,5-diyl)
Poly(3-cyclohexyl-4-methylthiophene-2,5-diyl)
Poly(3-cyclohexylthiophene-2,5-diyl)
Poly(3-decylthiophene-2,5-diyl)
Poly(3-dodecylthiophene-2,5-diyl)
Poly(3-hexylthiophene-2,5-diyl)
Poly(3-octylthiophene-2,5-diyl)
Thiophene Oligothiophenes
5,5'-Dibromo-2,2'-bithiophene, optionally 99%
2,2',5',2''',5''',2''''-Quaterthiophene, optionally 96%
α-Sexithiophene
311073 2,2':5',2''-Terthiophene, optionally 99%
Poly(thiophene-2,5-diyl), bromine terminated powder
2,3-Dihydrothieno[3,4-b]-1,4-dioxin
3,2':5',3''-Terthiophene
5-Hexyl-2,2'-bithiophene
22,2'-Bithiophene
Thiophene
5,5''-Dihexyl-2,2':5',2'':5'',2''':5''',2'''':5'''',2'''''-sexithiophene
Poly(styrenesulfonate)/poly(2,3-dihydrothieno(3,4-b)-1,4-dioxin)
Poly(3,4-ethylenedioxythiophene)-poly(styrenesulfonate)
Poly(3,4-ethylenedioxythiophene)-block-poly(ethylene glycol)
Poly(3,4-ethylenedioxythiophene), tetramethacrylate end-capped
Poly((9,9-dihexyl-9H-fluorene-2,7-diyl)-co-(1-methoxy-4-(2-ethylhexyloxy)-2,5-phenylenevinylene))
Poly(1-methoxy-4-(3-propyloxy-heptaisobutyl-PSS)-2,5-phenylenevinylene)-co-(1-methoxy-4-(2-ethylhexyloxy)-2,5-phenylenevinylene)
Poly(2,5-bis(3-sulfonatopropoxy)-1,4-phenylene, disodium salt-alt-1,4-phenylene)
Poly(2,5-dihexyloxy-1,4-phenylenevinylene)
Poly(2,5-dioctyl-1,4-phenylenevinylene)
Poly(2,6-naphthalenevinylene)
Poly[5-methoxy-2-(3-sulfopropoxy)-1,4-phenylenevinylene] Potassium salt
Poly(p-xylene tetrahydrothiophenium chloride)
Poly[(m-phenylenevinylene)-alt-(2-methoxy-5-octyloxy-p-phenylenevinylene)]
Poly[(m-phenylenevinylene)-alt-(2,5-dihexyloxy-p-phenylenevinylene)]
Poly[(m-phenylenevinylene)-alt-(2-methoxy-5-(2-ethylhexyloxy)-p-phenylenevinylene)]
Poly[(m-phenylenevinylene)-co-(2,5-dioctoxy-p-phenylenevinylene)]
Poly[(m-phenylenevinylene)-alt-(2,5-dibutoxy-p-phenylenevinylene)]
Poly[(o-phenylenevinylene)-alt-(2-methoxy-5-(2-ethylhexyloxy)-p-phenylenevinylene)]
Poly[(p-phenylenevinylene)-alt-(2-methoxy-5-(2-ethylhexyloxy)-p-phenylenevinylene)]
Poly[2-(2',5'-bis(2''-ethylhexyloxy)phenyl)-1,4-phenylenevinylene]
Poly[2,5-bis(3',7'-dimethyloctyloxy)-1,4-phenylenevinylene]
Poly[(2,5-bisoctyloxy)-1,4-phenylenevinylene]
Poly[2-methoxy-5-(2-ethylhexyloxy)-1,4-phenylenevinylene]
Poly[2-methoxy-5-(3',7'-dimethyloctyloxy)-1,4-phenylenevinylene]
Poly[5-methoxy-2-(3-sulfopropoxy)-1,4-phenylenevinylene]
Poly[9-(2-ethylhexyl)-3,6-carbazolevinylene-alt-2,6-naphthalenevinylene]
Poly{[2-[2',5'-bis(2''-ethylhexyloxy)phenyl]-1,4-phenylenevinylene]-co-[2-methoxy-5-(2'-ethylhexyloxy)-1,4-phenylenevinylene]}
or a combination of any two or more thereof.

When the polymer is a copolymer, it will be understood that any molar ratio of two substantially water-insoluble conjugated polymers may be used in any given copolymer. Preferred molar ratios are:

[Poly[(9,9-di-(2-ethylhexyl)-9H-fluorene-2,7-diyl)-co-(1-methoxy-4-(2-ethylhexyloxy)-2,5-phenylenevinylene)], 90:10 mole ratio
[Poly((9,9-di-(2-ethylhexyl)-9H-fluorene-2,7-diyl)-co-(1-methoxy-4-(2-ethylhexyloxy)-2,5-phenylenevinylene)], 95:5 mole ratio
Poly((9,9-dihexyl-9H-fluorene-2,7-diyl)-co-(1-methoxy-4-(2-ethylhexyloxy)-2,5-phenylenevinylene), 90:10 mole ratio
Poly((9,9-dihexyl-9H-fluorene-2,7-diyl)-co-(1-methoxy-4-(2-ethylhexyloxy)-2,5-phenylenevinylene)), 95:5 mole ratio
Poly((9,9-dihexyl-9H-fluorene-2,7-diyl)-co-(1-methoxy-4-(2-ethylhexyloxy)-2,5-phenylenevinylene), 90:10 mole ratio
Poly((9,9-dihexyl-9H-fluorene-2,7-diyl)-co-(1-methoxy-4-(2-ethylhexyloxy)-2,5-phenylenevinylene)), 95:5 mole ratio
Poly(1-methoxy-4-(3-propyloxy-heptaisobutyl-PSS)-2,5-phenylenevinylene)-co-(1-methoxy-4-(2-ethylhexyloxy)-2,5-phenylenevinylene) 60:40 mole ratio It will be appreciated that any biocompatible surfactant and/or lipid can be used to provide the conjugated polymer with its water solubility; further one or more surfactants and/or lipids may be used alone or in combination. For instance, a plurality of surfactants and/or lipids may be used together, in some examples there will be one, two, three or four surfactants and/or lipids forming the shell of the micellar structure.

According to one embodiment of the invention, the surfactant comprises a hydrophilic polymer which can comprise at least two monomers. The maximum number of monomers can be any number which forms a micelle having a diameter of approximately 5 nm to approximately 45 nm. Preferably, the maximum number of monomers comprising the polymer is 1000, more preferably 900, even more preferably 800, and most preferably 700 monomers.

Non-limiting examples of hydrophilic polymers include, but are not limited to, polystyrene sulfonic acid, poly-N-alkylvinylpyridinium halogenide, poly(meth)acrylic acid, poly(amino acids), poly-N-vinylpyrrolidone, polyhydroxyethyl methacrylate, polyvinylether, polyethylene glycol, polypropylene oxide, poly(maleic anhydride-alt-1-octadecene), polystyrene-b-polyacrylic acid, poly(methyl methacrylate)-poly(ethylene oxide), hyperbranched polyethyleneimine, peptides, and polysaccharides such as agarose, dextran, starch, cellulose, amylose, amylopectin, and starch, or any combination or derivative thereof.

According to another embodiment of the invention, the hydrophilic moiety comprises polyethylene glycol (PEG) or polyethylene imine chains. The polyethylene glycol or polyethylene imine chain can be any molecular mass which can form a micelle having a diameter of approximately 5 to approximately 45 nm. Preferably, the minimum average molecular mass for polyethylene glycol or polyethylene imine is about 350 Da, more preferably about 550 Da, even more preferably about 750 Da, and most preferably about 1000 Da.

Further exemplary surfactants include, but are not limited to:

Anionic surfactants such as those based on sulfate, sulfonate or carboxylate anions, such as but not limited to sodium dodecyl sulfate (SDS), ammonium lauryl sulfate, and other alkyl sulfate salts, sodium laureth sulfate, sodium lauryl ether sulfate (SLES), alkyl benzene sulfonate, sodium cholate, sodium deoxycholate, N-lauroylsarcosine sodium salt, lauryldimethylamine-oxide (LDAO), bis(2-ethylhexyl) sulfosuccinate sodium salt, cholic acid sodium salt, dodecyl sulfate (lithium or sodium salts), soaps, and fatty acid salts.

Cationic surfactants (based on quaternary ammonium cations) such as but not limited to cetyl trimethylammonium bromide, hexadecyl trimethyl ammonium bromide, and other alkyltrimethylammonium salts, cetylpyridinium chloride, polyethoxylated tallow amine, benzalkonium chloride, benzethonium chloride, palmityl trimethylammonium bromide, (2-hydroxyethyl)trimethylammonium chloride.

Zwitterionic surfactants (amphoteric), such as but not limited to dodecyl betaine, dodecyl dimethylamine oxide, cocamidopropyl betaine, coco ampho glycinate.

Nonionic surfactants, such as but not limited to polyethylene glycol, alkyl poly(ethylene oxide), copolymers of poly (ethylene oxide) and poly(propylene oxide) (commercially called poloxamers or poloxamines), alkyl polyglucosides, including: octyl glucoside, decyl maltoside, fatty alcohols, cetyl alcohol, oleyl alcohol, cocamide MEA, cocamide DEA, cocamide TEA, bishydroxyethylether, N,N-dimethyldecylamine-N-oxide, N,N-dimethyldodecylamine-N-oxide, 1,6-hexanediol, or ethylene glycol octyl phenyl ether (Triton® X-100 solution).

Preferably, the surfactant used is a PEG-based surfactant or SDS. PEG-based surfactants are especially preferred as they are biologically inert and reduce non-specific binding. Of the PEG-based surfactants, PEG-based phospholipids are often used.

According to a particular embodiment of the invention, the lipid comprises a phospholipid. It is presently generally preferred that the micelle comprise a lipid, often a phospholipid. The lipid or phospholipid may be used alone, in combination with other lipids/phospholipids or in combination with surfactants such as those listed above. There will often be a single phospholipid in the shell of the micelle; however, two, three or more may be used, or the phospholipid may be used with one, two, three or more lipids of other types, or surfactants.

Non-limiting examples of a phospholipid include any glyceryl ester of phosphoric acid wherein the glycerol backbone is further linked by ester bonds to two fatty acyl moieties. In a particular embodiment, the phosphate group of the phospholipid is bound by a ester link to an ethanolamine. This phospholipid is referred to as 1,2-di(fatty acyl)-sn-glycero-3-phosphoethanolamine, also known as phosphatidylethanolamine (PE). The fatty acyl moieties can comprise a hydrocarbon chain, and may be the same or different.

The hydrocarbon chain may be saturated or unsaturated, straight-chain or branched, substituted or unsubstituted. Examples of saturated or unsaturated hydrocarbon chains include n-dodecyl, n-tetradecyl, n-hexadecyl, n-octadecyl, and n-icosyl, oleyl, linoleyl, linolenyl and eleostearyl.

When the hydrocarbon chains are substituted, they are preferably substituted by a $C_1$-$C_4$ alkyl, alkenyl, or alkynyl group, such as methyl, ethyl, propyl, isopropyl, n-butyl, t-butyl, isobutyl, ethenyl, propenyl, butadienyl, isobutenyl, ethynyl, propynyl or butynyl. Examples of branched hydrocarbon chains include 3,7,11,15-tetramethylhexadecyl and cis or trans 3,7,11,15-tetramethyl-2-hexadecenyl.

Any of the carbon atoms in any of the hydrocarbon chains described above may further comprise a hydrocarbon ring structure, which may be saturated or unsaturated. Non-limiting examples of hydrocarbon rings include cyclopentyl, cyclopentenyl, cyclohexyl, and phenyl, and an example of hydrocarbon chains further comprising hydrocarbon rings includes 1-butyl-4-cyclohexyl-12-dodecyl.

Further exemplary lipids include n-poly(ethylene glycol) phosphatidylethanolamine (PEG-PE), phosphatidylcholine (PC), phosphatidic acids, Phosphatidylglycerol, phosphatidylserine, phosphatidylinositol, bis(Monoacylglycero)phosphate, cardiolipin, ether lipids, plasmalogens, and/or sphingolipids.

Further, the lipid may be a paramagnetic lipid, such as Gd-DTPA-bis(stearylamide), and as such may exhibit magnetic activity independently of the MRI active agent.

Also provided by the invention is a composition comprising a substantially water-insoluble conjugated polymer which exhibits luminescence or fluorescence within the wavelength band from about 300 nm to about 1500 nm of the electromagnetic spectrum, a biocompatible surfactant and/or lipid, wherein the substantially water-insoluble conjugated polymer is selected from:

Poly[9,9-di(3',7'-dimethyloctyl)fluoren-2,7-yleneethynylene]
Poly[9,9-didodecylfluroenyl-2,7-yleneethylnylene]
Poly[9,9-di(2'-ethylhexyl)fluoren-2,7-yleneethynylene]
Poly(9,9-dioctylfluorenyl-2,7-yleneethynylene
Poly[9,9-bis-(2-ethylhexyl)-9H-fluorene-2,7-diyl]
Poly(9,9-dihexyl-9H-fluorene-2,7-diyl)
Poly(9,9-di-(2-ethylhexyl)-9H-fluorene-2,7-diyl)
Poly[(9,9-di-(2-ethylhexyl)-9H-fluorene-2,7-diyl)-co-(1-methoxy-4-(2-ethylhexyloxy)-2,5-phenylenevinylene)]
Poly((9,9-dihexyl-9H-fluorene-2,7-diyl)-co-(1-methoxy-4-(2-ethylhexyloxy)-2,5-phenylenevinylene))
Poly(2,5-bis(1,4,7,10-tetraoxaundecyl)-1,4-phenylenevinylene)
Poly(2,5-dioctyl-1,4-phenylenevinylene)

Poly(2,5-dioctylphenylene-1,4-ethynylene)
Poly[1,2-bis(benzylthio)acetylene]
Poly[1,2-bis(ethylthio)acetylene]
Poly[bis(methylthio)acetylene]
Poly(3,5 pyridine)
Poly(3-(2-methoxyethoxy)ethoxymethylthiophene-2,5-diyl)
5,5'-Dibromo-2,2'-bithiophene
Poly(3-butylthiophene-2,5-diyl)
Poly(3-cyclohexyl-4-methylthiophene-2,5-diyl)
Poly(3-cyclohexylthiophene-2,5-diyl)
Poly(3-decylthiophene-2,5-diyl)
Poly(3-dodecylthiophene-2,5-diyl)
Poly(3-hexylthiophene-2,5-diyl)
Poly(3-octylthiophene-2,5-diyl)
Thiophene Oligothiophenes
5,5'-Dibromo-2,2'-bithiophene
2,2',5',2'',5'',2''''-Quaterthiophene
α-Sexithiophene
311073 2,2':5',2''-Terthiophene
Poly(thiophene-2,5-diyl), bromine terminated powder
2,3-Dihydrothieno[3,4-b]-1,4-dioxin
3,2':5',3''-Terthiophene
5-Hexyl-2,2'-bithiophene
22,2'-Bithiophene
Thiophene
5,5''''-Dihexyl-2,2':5',2'':5'',2''':5''',2'''':5'''',2'''''-sexithiophene
Poly(styrenesulfonate)/poly(2,3-dihydrothieno(3,4-b)-1,4-dioxin)
Poly(3,4-ethylenedioxythiophene)-poly(styrenesulfonate)
Poly(3,4-ethylenedioxythiophene)-block-poly(ethylene glycol)
Poly(3,4-ethylenedioxythiophene), tetramethacrylate end-capped
Poly((9,9-dihexyl-9H-fluorene-2,7-diyl)-co-(1-methoxy-4-(2-ethylhexyloxy)-2,5-phenylenevinylene))
Poly((9,9-dihexyl-9H-fluorene-2,7-diyl)-co-(1-methoxy-4-(2-ethylhexyloxy)-2,5-phenylenevinylene)
Poly(1-methoxy-4-(3-propyloxy-heptaisobutyl-PSS)-2,5-phenylenevinylene)-co-(1-methoxy-4-(2-ethylhexyloxy)-2,5-phenylenevinylene)
Poly(2,5-bis(3-sulfonatopropoxy)-1,4-phenylene, disodium salt-alt-1,4-phenylene)
Poly(2,5-dihexyloxy-1,4-phenylenevinylene)
Poly(2,5-dioctyl-1,4-phenylenevinylene)
Poly(2,6-naphthalenevinylene)
Poly[5-methoxy-2-(3-sulfopropoxy)-1,4-phenylenevinylene] Potassium salt
Poly(p-xylene tetrahydrothiophenium chloride)
Poly[(m-phenylenevinylene)-alt-(2-methoxy-5-octyloxy-p-phenylenevinylene)]
Poly[(m-phenylenevinylene)-alt-(2,5-dihexyloxy-p-phenylenevinylene)]
Poly[(m-phenylenevinylene)-alt-(2-methoxy-5-(2-ethylhexyloxy)-p-phenylenevinylene)]
Poly[(m-phenylenevinylene)-co-(2,5-dioctoxy-p-phenylenevinylene)]
Poly[(m-phenylenevinylene)-alt-(2,5-dibutoxy-p-phenylenevinylene)]
Poly[o-phenylenevinylene)-alt-(2-methoxy-5-(2-ethylhexyloxy)-p-phenylenevinylene)]
Poly[p-phenylenevinylene)-alt-(2-methoxy-5-(2-ethylhexyloxy)-p-phenylenevinylene)]
Poly[2-(2',5'-bis(2''-ethylhexyloxy)phenyl)-1,4-phenylenevinylene]
Poly[2,5-bis(3',7'-dimethyloctyloxy)-1,4-phenylenevinylene]
Poly[(2,5-bisoctyloxy)-1,4-phenylenevinylene]
Poly[2-methoxy-5-(2-ethylhexyloxy)-1,4-phenylenevinylene]
Poly[2-methoxy-5-(3',7'-dimethyloctyloxy)-1,4-phenylenevinylene]
Poly[5-methoxy-2-(3-sulfopropoxy)-1,4-phenylenevinylene]
Poly[9-(2-ethylhexyl)-3,6-carbazolevinylene-alt-2,6-naphthalenevinylene]
Poly{[2-[2',5'-bis(2''-ethylhexyloxy)phenyl]-1,4-phenylenevinylene]-co-[2-methoxy-5-(2'-ethylhexyloxy)-1,4-phenylenevinylene]},
or a combination of any two or more thereof; and
an MRI active agent.

In a typical example, MEH-PPV and an MRI active agent such as iron oxide ($Fe_3O_4$), can be processed into micelles encased by a phospholipid, which is a water-soluble and biologically inert material often used in biology. The water-soluble micelles of MEH-PPV/iron oxide still exhibit a strong red emission and can readily be used in imaging applications. The materials are extremely stable (exhibiting stability under excitation exceeding that of a commercially available dye), still exhibiting luminescent properties months after being prepared and stored in ambient conditions.

The presence of the MRI active agent allows detection using MRI imaging, and magnetic techniques; providing a labelling composition which can be analysed in more than one way using a single sample. This facilitates the application of multiple analytical techniques to the sample, reducing the need to inconvenience the patient, and increasing analysis and hence diagnosis times. Further, the magnetic properties of the MRI active agent offer the potential for the labelling and/or separation of substances; for instance from the substrate to which they are attached at crime scenes. This separation can be beneficial as it allows for a quantitative analysis of the substance, with a greater sensitivity as the substrate is no longer present to obscure the analytical results, used in combination with the ability to image the substance using the fluorescence emission of the LEP, in real time at the crime scene, the micellar compositions of the invention offer a significant advance in crime scene detection technology.

The micelles of the composition used in the invention are typically in the range about 5 and about 1000 nm in diameter, often in the range about 5 to about 100 nm in diameter.

According to one embodiment of the invention, a plurality of substantially water-insoluble conjugated polymers may be used in the composition, which may be two or more, or three or more polymers in combination.

The MRI active agent of the invention may be any MRI active agent, as would be familiar to the person skilled in the art. Such agents include, but are not limited to, iron oxide (FeO, $Fe_2O_3$, $Fe_3O_4$), including both superparamagnetic iron oxide (SPIO) and ultrasmall superparamagnetic iron oxide (USPIO); other metal oxides and metal oxide heterostructures such as MnO, M-$Fe_3O_4$ (M=Fe, Au, Ag) or $MFe_2O_4$ (M=Ni, Co, Mn); metal particles such as Fe, FePt, Co and FeCo; and gadolinium complexes such as $Gd_2O_3$, $GdF_3$ and $NaGdF_4$. In many instances metal oxides are used, in particular iron oxides such as $Fe_3O_4$.

The MRI active agent may comprise a single MRI active agent or a plurality of MRI active agents used in combination, for instance, there may be one, two, three or four different MRI active agents present in the micellar composition of the invention. In some embodiments of the invention the core of the micelle will include a metal oxide MRI active agent, and a second (or a plurality of) MRI active agent(s). This second MRI active agent may be selected from gadolinium, iron or manganese complexes such as those listed above.

The MRI active agent may be randomly distributed throughout the polymer core, or may be distributed within the core such that it is generally present towards the outer surface of the core. In some instances, the MRI active agent will be present in a layer around the polymer core, in some cases the MRI active agent could be said to encapsulate the core, with the biocompatible surfactant and/or lipid encapsulating the core of MRI active agent and water-insoluble conjugated polymer. It has been observed, however, that regardless of the internal structure of the core, the luminescence/fluorescence properties of the conjugated polymer are not impaired by the presence of the MRI active agent and vice versa. As such, the micellar compositions of the invention offer a truly multi-modal composition, of a type not previously available.

The presence of the MRI active agent is useful in allowing multimodal analysis of the substances being detected, whether the composition is being used in biological labelling, or to bind to and detect or separate a substance from other substances under, for instance, crime scene circumstances.

The micelles of the invention may additionally comprise optional components such as dopants to enhance the emission properties of the water-insoluble conjugated polymer (such as, but not limited to, organic dopants such as rubrene, inorganic dopants such as iridium complexes, rare-earth materials), or semiconductor quantum dots such as ZnS, ZnSe, ZnTe, Mn doped Zn based quantum dots (wherein the Zn component is typically ZnS, ZnSe or ZnTe), InP, GaP, InGaP, or a combination thereof. Examples of rare-earth materials include organolanthanide complexes or rare-earth containing nanoparticles such as $Y_2O_3$:Eu, rare-earth fluorides, or phosphates.

According to another embodiment of the invention, the water-insoluble conjugated polymers may be encased in an inert biologically compatible material after being contacted with a biocompatible surfactant and/or lipid. Exemplary biologically compatible materials include silica, PMMA, latex or polystyrene.

According to another embodiment of the invention, a shell of another substantially water-insoluble conjugated polymer may be deposited onto the surface of the water-insoluble conjugated polymer. This polymer may be any other substantially water-insoluble conjugated polymer which has a wider band (or energy) gap than the original water-insoluble conjugated polymer, forming a core/shell system. The core/shell system is then encased by a biocompatible surfactant and/or lipid. This wider band gap aids in preventing the charge carrying groups in the original water-insoluble conjugated polymer from escaping and generating undesirable free radicals.

Examples of such polymers include polymers having at least two monomers. The maximum number of monomers can be any number which forms a micelle having a diameter of approximately 5 nm to approximately 45 nm. Preferably, the maximum number of monomers comprising the polymer is 1000, more preferably 900, even more preferably 800, and most preferably 700 monomers.

Each monomer comprises at least one oxygen or nitrogen atom, and may include more, such as two, five, or ten oxygen or nitrogen atoms. Examples of monomers useful in the invention include N-alkylacrylamide, N,N-dialkylacrylamide, N-isopropylacrylamide, N-methylacrylamide, N-ethylmethacrylamide, N,N-propylacrylamide, N,N-propylmethacrylamide, N-isopropylmethacrylamide, N-cyclopropylacrylamide, N,N-diethylacrylamide, N-methyl-N-isopropylacrylamide, N-methyl-N,N-propylacrylamide, propylene oxide, vinyl ether, hydroxyethyl methacrylate, N-vinylpyrrolidone, amino acids, methacrylic acid, N-alkylvinylpyridinium halogenide, styrene sulfonic acid, ethylene glycol, and monosaccharides such as glucose, galactose, mannose, and fructose.

Examples of polymers include, but are not limited to, polystyrene sulfonic acid, poly-N-alkylvinylpyridinium halogenide, poly(meth)acrylic acid, poly(amino acids), poly-N-vinylpyrrolidone, polyhydroxyethyl methacrylate, polyvinylether, polyethylene glycol, polypropylene oxide, and polysaccharides such as agarose, dextran, starch, cellulose, amylose, amylopectin, and starch.

According to another embodiment of the invention, the surfactant shell (such as, but not limited to, PEG) may be modified by the addition of a biological linker. The linker may be selected from a non-limiting list of a protein, DNA, peptide, antibody, enzyme, biotin, carboxylic acid group, amine group, alcohol group, or a thiol group.

The addition of such a biological linker group is useful to enable the particles to be targeted at the labelling or detection of a specific material (such as a biological material) or substance. The target materials and substances could be cancer cells, organ tissue such that of a heart, liver or kidney, skin, blood, normal cells, drugs, drug metabolites, or explosives. However, a person using the 'bare' particles without a biological linker can use an anchor point on the surface of the particles to derivatise the particles with a specific linker as required for targeting any particular material or substance of interest.

Also provided in a seventh aspect of the invention is a kit for use in the labelling of biological material, the kit comprising a substantially water-insoluble conjugated polymer which exhibits luminescence or fluorescence from about 300 nm to about 1500 nm of the electromagnetic spectrum, a biocompatible surfactant and/or lipid, and a MRI active agent.

Alternatively, an eighth aspect of the invention relates to a kit for the detection of a substance on a substrate, the kit comprising: a composition as described in the first aspect of the invention; and instructions for the use of the composition in the method the sixth aspect of the invention.

Substrates that may be tested using the detection process of the present invention include, but are not limited to, paper, glass, plastic, wood, metal, cloth. Examples of such substrates include, but are not limited to, documents, wallpaper, sheets and clothing.

The composition of the invention may be applied to the substrate by brushing or spraying the formulation onto the surface of the substrate. Separation will generally be through the use of simple magnets, passed in proximity to the substrate. Once the substance/micelle complex has been transferred to the magnet, this may be simply washed to remove the sample for further testing. Alternatively, the sample may be analysed in situ, on the magnet or on the substrate by, for instance, excitation with a UV lamp.

The micellar compositions of the invention may be used to detect any substance with which they will interact, or with which they can be modified (for instance through the addition of biological linkers), to interact. As noted above, such substances include drugs, drug metabolites, hormones, explosives and biological fluids such as semen, blood and saliva.

These may include: anabolic agents, Erythropoietin (EPO), Growth. Hormone (hGH), Insulin-like Growth Factors (e.g. IGF-I), Mechano Growth Factors (MGFs), Gonadotrophins (LH, hCG), beta-2 agonists, agents with anti-oestrogenic activity, diuretics, agents for the enhancement of oxygen transfer, stimulants, narcotics, cannabinoids, glucocorticosteriods, alcohol, beta-blockers, amphetamines, alkaloids and their derivatives, benzodiazepines, GHB and derivatives; examples of which include cocaine; benzoyl ecgonine; nicotine; cotinine, testosterone, oestrogen, TNT and RDX, and the metabolites of the above.

The micellar composition of the invention may be applied to body fluid stains and/or fingerprints known to contain the target substance. Sweat may be deposited on a substrate by means such as a taking a fingerprint from the subject. By testing for drugs or their metabolites in the sweat/body fluid stains, it is possible to determine whether a drug has been ingested by the subject, or simply handled. If a drug has been ingested by a subject, the drug and/or its metabolite will be present in a subject's excreted sweat/body fluid stains. However, if the drug had been handled, but not ingested, the drug may be present on a subject's skin, and may be transferred to, for example, the subject's fingerprint.

According to another embodiment of the invention, the water-insoluble conjugated polymers may be linked to other species which exhibit luminescence or fluorescence within the wavelength band from about 300 nm to about 1500 nm of the electromagnetic spectrum (such as but not limited to dyes, luminescent proteins, quantum dots) for FRET (Fluorescence lifetime and Resonance Energy Transfer) imaging applications.

According to another aspect of the invention, the micelles of the composition are used as free radical generators in photodynamic therapy applications.

Substantially water-insoluble conjugated polymers having a broad range of emissions are commercially available, and those used in the invention are capable of exhibiting several different colours of emission covering all of the visible and near infra-red parts of the electromagnetic spectrum, without amending their chemistry. It would therefore be possible to build up a palette of substantially water-insoluble conjugated polymers covering the desired emitted colours.

The invention will now be explained in more detail with reference to the accompanying Figures and the following Examples, which are merely illustrative and are in no way intended to limit the scope of the invention.

Figure 2:
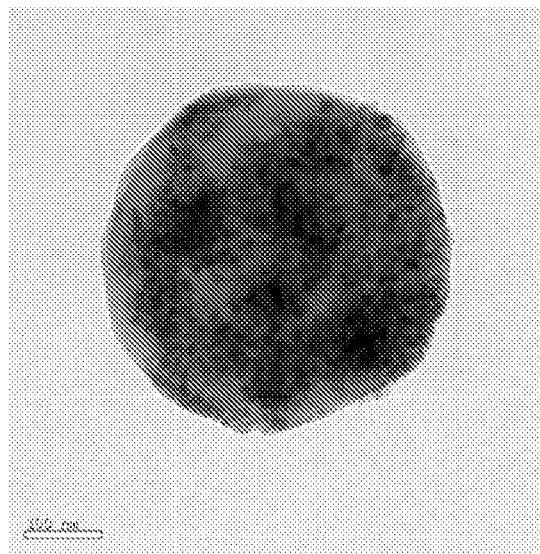
Figure 3:
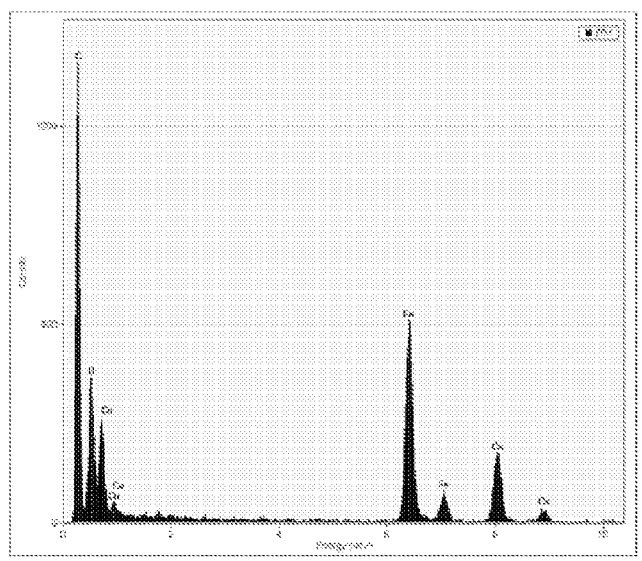

FIG. 1. is a TEM of the composition of Example 1 having particles of between 50 and 500 nm in diameter;

FIG. 2. is a high resolution electron microscope image of the composition of Example 1;

FIG. 3. is an EDX analysis of the composition of Example 1; and

Figure 4:
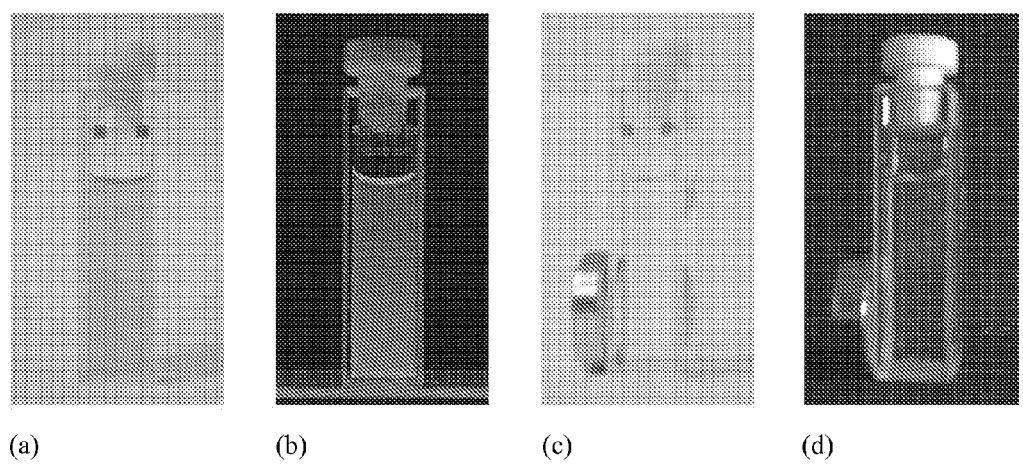

FIGS. 4(*a*) to (*d*) show samples of the composition of Example 1 (a) under natural light, (b) excited with a UV lamp (365 nm), (c) under natural light, next to a magnet, and (d) excited with a UV lamp (365 nm) and next to a magnet.

EXAMPLE 1

Method for the Preparation of Micelles

In a typical example, 0.85 mg of MEH-PPV (Poly[2-methoxy-5-(2-ethylhexyloxy)-1,4-phenylene vinylene], Mn=40,000-70,000, Sigma-Aldrich) was dissolved in 16 ml of dichloromethane and stirred for 2 days to ensure complete dissolution of the polymer. 300 µl of $Fe_3O_4$ nanoparticles in heptane (07318 BioChemika) was added to the MEH-PPV solution. This was stirred in a vial for 10 minutes. 6.8 mg PEG2000-PE (1,2-Diacyl-sn-Glycero-3-Phosphoethanolamine-N-[Methoxy(Polyethylene glycol)-2000], Avanti Lipids) and 2.6 mg DPPC (1,2-Dipalmitoyl-sn-Glycero-3-Phosphocholine, Avanti Lipids) were then added, and the solution was stirred for a further 10 minutes. This solution was added to 20 ml of water and stirred vigorously in a beaker for 1 hour. After evaporation of the DCM a dark red translucent solution remained. The product was filtered through paper and stored. A TEM of the particles obtained is shown in FIG. 1 and an electron microscope image in FIG. 2.

EXAMPLE 2

Method for the Preparation of Micelles

In another example, micelles of the same composition were prepared using an alternative method. 0.85 mg of MEH-PPV was added to 16 ml DCM and stirred for 2 days to obtain complete dissolution of the polymer. The polymer solution was filtered through a 0.2 µm filter prior to the addition of 7 mg of $PEG_{2000}$-PE and 3 mg of DPPC. 0.1 ml of iron oxide nanoparticles in heptane (07318 BioChemika) was added, and the solution was shaken for 10 minutes. The DCM solution was added to 30 ml water under ultrasound and vigorous stirring. The ultrasound was turned off after 1 minute, and stirring continued for a further 7 minutes until the solution became transparent red. No precipitation occurred during the synthesis. The solution was then filtered through filter paper. The magnetic nanoparticles were then collected by magnetic filtration, and the supernatant was discarded.

The compositions of both Example 1 and Example 2 were simply prepared and required no complex chemistry. The strategies can in theory be extended to all commercially available semi-conducting polymers and represents a new class of biological labels.

EXAMPLE 3

The EDX spectrum shown in FIG. 3 clearly indicates the presence of iron in the micellar structure of the composition.

The spectrum of FIG. 3 was prepared using an FEI Tecnai 20 at 200 kV for high resolution imaging. The samples were drop cast and dried on carbon film copper grids. High resolution elemental analysis was performed by analysis of EDX spectra collected using an EDAX spectrometer. The sample was cooled with liquid nitrogen and analyzed under vacuum.

EXAMPLE 4

FIG. 4 shows the micelles of Example 1 in use. Specifically, FIG. 4(*a*) shows a cuvette containing the inventive micelles under normal lighting conditions, and when excited with UV light (FIG. 4(*b*)), the conjugated polymer in the core of the micelle emits a strong fluorescence signal which can be clearly seen despite the presence of the MRI active agent and the phospholipid shell. FIGS. 4(*c*) and (*d*) show the magnetic properties of the micelles, which clearly migrate to the area of the cuvette nearest to the magnetic source. This shows that the MRI active agent can fully interact with its surroundings despite the presence of the conjugated polymer and phospholipid shell. Finally, FIG. 4(*d*) shows a cuvette in which the micelles are clearly exhibiting both modes of reporting at the same time, as they are gathered near to the magnetic source, and also fluorescing.

The invention claimed is:
1. A micellar composition comprising:
   a substantially water-insoluble polymer having a conjugated backbone, wherein the conjugated backbone exhibits luminescence or fluorescence from about 300 nm to about 1500 nm of the electromagnetic spectrum;

a biocompatible surfactant and/or lipid; and
a MRI active agent;
wherein the substantially water-insoluble polymer and the MRI active agent are enveloped in the biocompatible surfactant and/or lipid, forming a micelle.

2. The composition according to claim 1, wherein the composition comprises more than one substantially water-insoluble conjugated polymer.

3. The composition according to claim 1, wherein the substantially water-insoluble conjugated polymer is selected from:
Poly[9,9-di(3',7'-dimethyloctyl)fluoren-2,7-yleneethynylene],
Poly[9,9-didodecylfluroenyl-2,7-yleneethylnylene],
Poly[9,9-di(2'-ethylhexyl)fluoren-2,7-yleneethynylene],
Poly(9,9-dioctylfluorenyl-2,7-yleneethynylene),
Poly[9,9-bis-(2-ethylhexyl)-9H-fluorene-2,7-diyl],
Poly(9,9-dihexyl-9H-fluorene-2,7-diyl),
Poly(9,9-di-(2-ethylhexyl)-9H-fluorene-2,7-diyl),
Poly[(9,9-di-(2-ethylhexyl)-9H-fluorene-2,7-diyl)-co-(1-methoxy-4-(2-ethylhexyloxy)-2,5-phenylenevinylene)],
Poly[(9,9-dihexyl-9H-fluorene-2,7-diyl)-co-(1-methoxy-4-(2-ethylhexyloxy)-2,5-phenylenevinylene)],
Poly(2,5-bis(1,4,7,10-tetraoxaundecyl)-1,4-phenylenevinylene),
Poly(2,5-dioctyl-1,4-phenylenevinylene),
Poly(2,5-dioctylphenylene-1,4-ethynylene),
Poly(3-(2-methoxyethoxy)ethoxymethylthiophene-2,5-diyl),
Poly(3-butylthiophene-2,5-diyl),
Poly(3-cyclohexyl-4-methylthiophene-2,5-diyl),
Poly(3-cyclohexylthiophene-2,5-diyl),
Poly(3-decylthiophene-2,5-diyl),
Poly(3-dodecylthiophene-2,5-diyl),
Poly(3-hexylthiophene-2,5-diyl),
Poly(3-octylthiophene-2,5-diyl),
Thiophene Oligothiophenes,
311073 2,2':5',2"-Terthiophene,
Poly(thiophene-2,5-diyl), bromine terminated powder,
Poly((9,9-dihexyl-9H-fluorene-2,7-diyl)-co-(1-methoxy-4-(2-ethylhexyloxy)-2,5-phenylenevinylene)),
Poly((9,9-dihexyl-9H-fluorene-2,7-diyl)-co-(1-methoxy-4-(2-ethylhexyloxy)-2,5-phenylenevinylene),
Poly(1-methoxy-4-(3-propyloxy-heptaisobutyl-PSS)-2,5-phenylenevinylene)-co-(1-methoxy-4-(2-ethylhexyloxy)-2,5-phenylenevinylene),
Poly(2,5-dihexyloxy-1,4-phenylenevinylene),
Poly(2,5-dioctyl-1,4-phenylenevinylene),
Poly(2,6-naphthalenevinylene),
Poly[(m-phenylenevinylene)-alt-(2-methoxy-5-octyloxy-p-phenylenevinylene)],
Poly[(m-phenylenevinylene)-alt-(2,5-dihexyloxy-p-phenylenevinylene)],
Poly[(m-phenylenevinylene)-alt-(2-methoxy-5-(2-ethylhexyloxy)-p-phenylenevinylene)],
Poly[(m-phenylenevinylene)-co-(2,5-dioctoxy-p-phenylenevinylene)],
Poly[(m-phenylenevinylene)-alt-(2,5-dibutoxy-p-phenylenevinylene)],
Poly[(o-phenylenevinylene)-alt-(2-methoxy-5-(2-ethylhexyloxy)-p-phenylenevinylene)],
Poly[(p-phenylenevinylene)-alt-(2-methoxy-5-(2-ethylhexyloxy)-p-phenylenevinylene)],
Poly[2-(2',5'-bis(2"-ethylhexyloxy)phenyl]-1,4-phenylenevinylene],
Poly[2,5-bis(3',7'-dimethyloctyloxy)-1,4-phenylenevinylene],
Poly[(2,5-bisoctyloxy)-1,4-phenylenevinylene],
Poly[2-methoxy-5-(2-ethylhexyloxy)-1,4-phenylenevinylene],
Poly[2-methoxy-5-(3',7'-dimethyloctyloxy)-1,4-phenylenevinylene],
Poly[5-methoxy-2-(3-sulfopropoxy)-1,4-phenylenevinylene],
Poly[9-(2-ethylhexyl)-3,6-carbazolevinylene-alt-2,6-naphthalenevinylene],
Poly{[2-[2',5'-bis(2"-ethylhexyloxy)phenyl]-1,4-phenylenevinylene]-co-[2-methoxy-5-(2'-ethylhexyloxy)-1,4-phenylenevinylene]}, and
a combination or any two or more thereof.

4. The composition according to claim 3, wherein the biocompatible surfactant is selected from anionic surfactants and nonionic surfactants, or the biocompatible lipid is selected from phospholipids and paramagnetic lipids.

5. The composition according to claim 4, wherein the biocompatible surfactant comprises polyethylene glycol or sodium dodecyl sulfate.

6. The composition according to claim 4, wherein the MRI active agent comprises $Fe_3O_4$, $Gd_2O_3$, $GdF_3$, $NaGdF_4$, MnO, $MnFe_2O_4$, $CoFe_2O_4$, $NiFe_2O_4$, Fe, FePt, FeCo, FeO, $Fe_2O_3$ or combinations thereof.

7. The composition according to claim 1, wherein the MRI active agent comprises $Fe_3O_4$, $Gd_2O_3$, $GdF_3$, $NaGdF_4$, MnO, $MnFe_2O_4$, $CoFe_2O_4$, $NiFe_2O_4$, Fe, FePt, FeCo, FeO, $Fe_2O_3$ or combinations thereof.

8. The composition according to claim 1, wherein the composition further comprises a dopant selected from rubrene, iridium complexes, rare-earth materials and ZnS, ZnSe, ZnTe, InP, GaP, InGaP, and Mn doped ZnE semiconductor quantum dots, wherein E is selected from S, Se and Te.

9. The composition according to claim 1, wherein the composition is encased in a layer of a biologically inert biocompatible material.

10. The composition according to claim 9, wherein the biologically inert biocompatible material is silica, poly(methyl methacrylate), latex or polystyrene.

11. The composition according to claim 9, comprising a layer of a further substantially water-insoluble conjugated polymer having a wider band gap than the substantially water-insoluble conjugated polymer between the substantially water-insoluble conjugated polymer and the biocompatible surfactant and/or lipid.

12. The composition according to claim 11, wherein the further polymer is selected from poly(methyl methacrylate), polystyrene sulfonic acid, poly-N-alkylvinylpyridinium halogenide, poly(meth)acrylic acid, poly(amino acids), poly-N-vinylpyrrolidone, polyhydroxyethyl methacrylate, polyvinylether, polyethylene glycol, polypropylene oxide, and polysaccharides, and a combination or derivative thereof.

13. The composition according to claim 1, wherein the biocompatible surfactant and/or lipid has been modified to selectively bind to a desired substance.

14. The composition according to claim 13, wherein the biocompatible surfactant and/or lipid has been modified by the addition of a protein, nucleic acid, enzyme, antibody, an amine group, a carboxylic acid group, an alcohol-containing group, a thiol group, or biotin.

15. The composition according to claim 13, wherein the substance is selected from drugs, metabolites, proteins, polypeptides, nucleic acids, cancer cells, organ tissue from a heart, liver or kidney, skin, blood or normal cells.

16. The composition according to claim 1, wherein the composition is linked to a further species which exhibits luminescence or fluorescence within the wavelength band from about 300 nm to about 1500 nm of the electromagnetic spectrum.

17. The composition according to claim 16, wherein the further species comprises a dye, a luminescent protein, or quantum dots selected from ZnS, ZnSe, ZnTe, InP, GaP, InGaP, and Mn doped Zn.

18. A method of labelling a biological material, comprising the steps of: providing a composition according to claim 1; and bringing the composition into contact with the biological material.

19. The method or use according to claim 18 wherein the labelling of a biological material is carried in vitro.

20. The biological material labelled by a composition according to claim 1.

21. A method for the detection of a substance, the method comprising:
   providing a composition according to claim 1;
   contacting the composition with the substance on a substrate; and
   fluorescent and/or magnetic resonance imaging the composition to determine whether the substance was present on the substrate.

22. The method of claim 21, and further comprising removing the composition from the substrate.

23. The method according to claim 21, wherein the substance is a biological substance, drug, or metabolite.

24. The method according to claim 21 wherein the substrate has a fingerprint of a human on a surface with which the particles are contacted.

* * * * *